United States Patent [19]

Gross

[11] Patent Number: 5,002,535
[45] Date of Patent: Mar. 26, 1991

[54] STEPPED NEEDLE

[75] Inventor: James R. Gross, St. Charles, Ill.

[73] Assignee: The Kendall Company, Boston, Mass.

[21] Appl. No.: 478,323

[22] Filed: Feb. 12, 1990

Related U.S. Application Data

[62] Division of Ser. No. 223,964, Jul. 25, 1988, Pat. No. 4,909,800, which is a division of Ser. No. 74,609, Jul. 17, 1987, Pat. No. 4,781,691.

[51] Int. Cl.⁵ .............................................. A61M 5/18
[52] U.S. Cl. ..................................... 604/164; 604/272
[58] Field of Search ........................ 604/164, 264, 272

[56] References Cited

U.S. PATENT DOCUMENTS

| | | | |
|---|---|---|---|
| 3,993,079 | 11/1976 | Gatztanondo | 604/164 |
| 4,202,332 | 5/1980 | Tertzegen | 604/164 |
| 4,405,314 | 9/1983 | Cope | 604/164 |
| 4,652,256 | 3/1987 | Vaillancourt | 604/164 |

FOREIGN PATENT DOCUMENTS 2408852  9/1975  Fed. Rep. of Germany ...... 604/272

Primary Examiner—John D. Yasko
Attorney, Agent, or Firm—Alvin Isaacs

[57] ABSTRACT

A stepped needle comprising, a proximal hollow hub, a first elongated tubular portion extending from the hub of a first larger diameter, and a second elongated tubular end portion located distal the first tubular portion of a second smaller diameter.

3 Claims, 2 Drawing Sheets

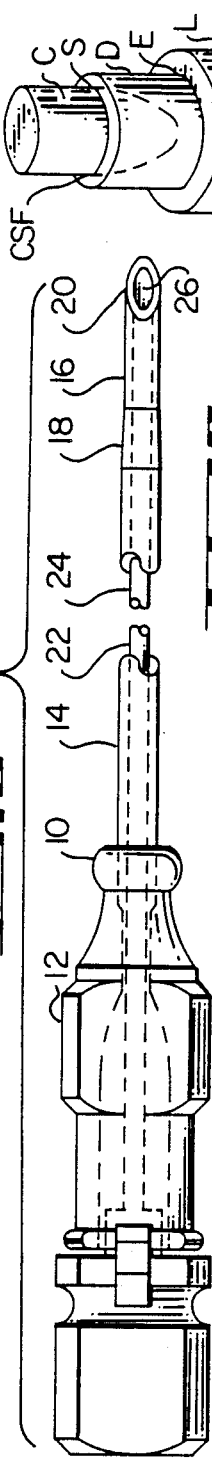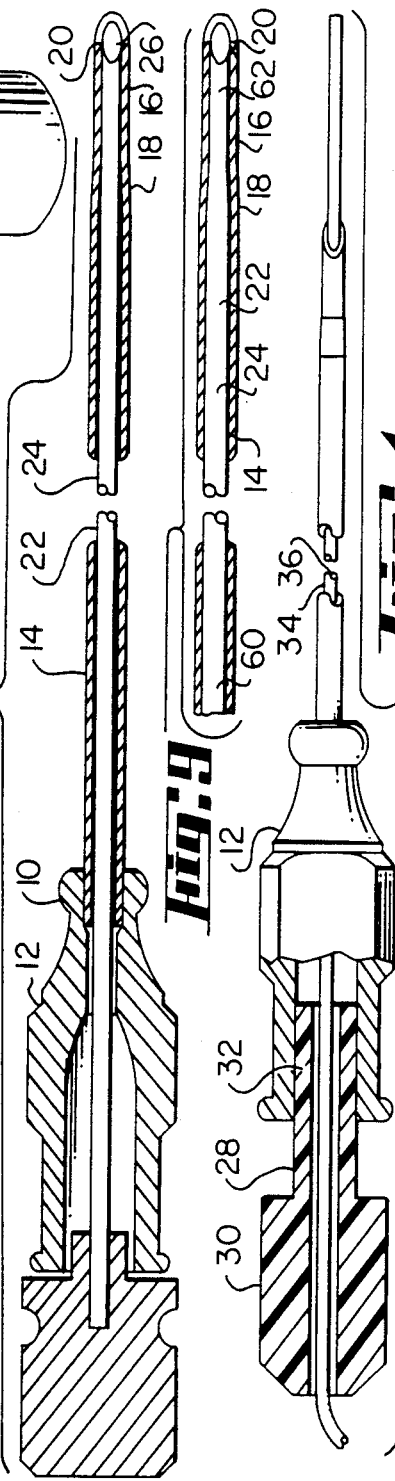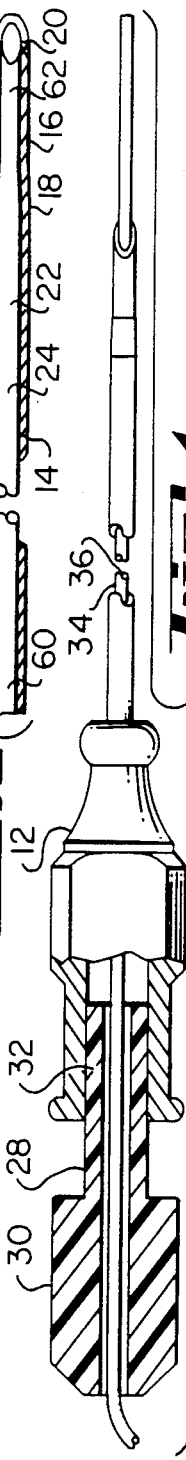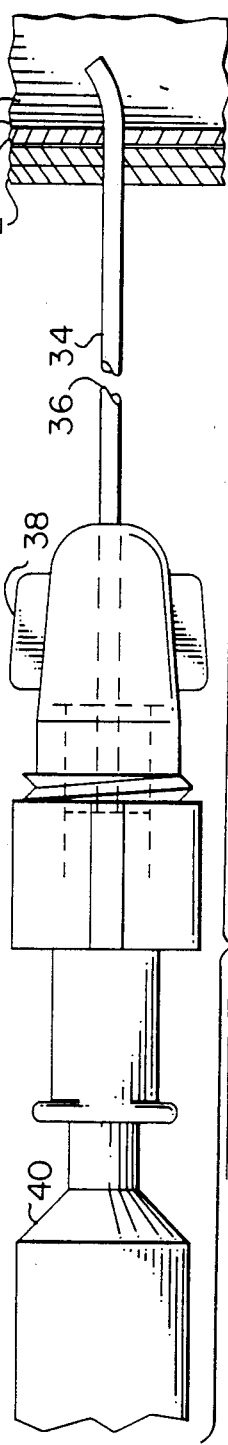

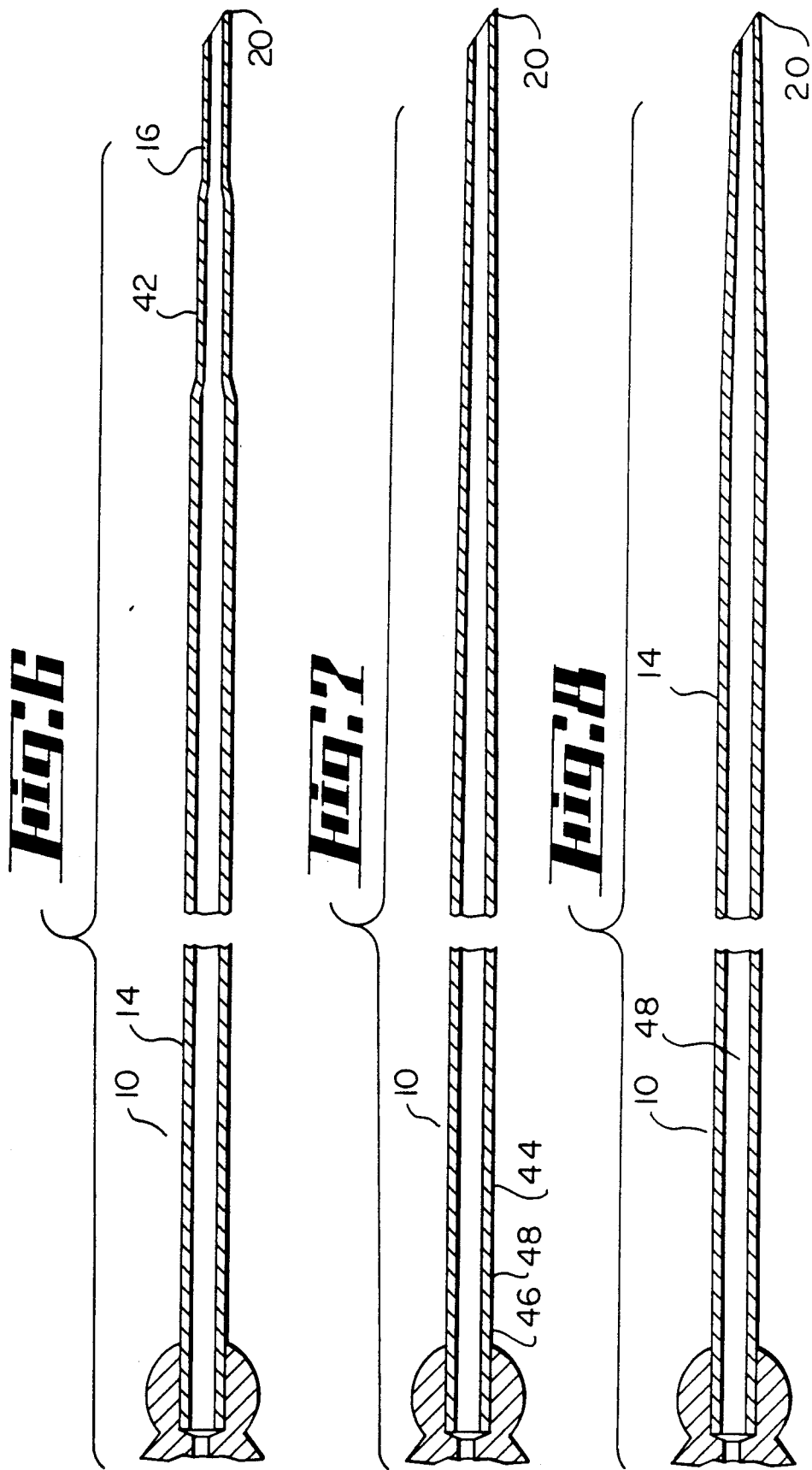

STEPPED NEEDLE

This is a division of application Ser. No.: 223,964, filed July 25, 1988, now U.S. Pat. No. 4,909,800 a divisional of Ser. No.: 074,609, filed July 17, 1987, now U.S. Pat. No. 4,781,691.

BACKGROUND OF THE INVENTION

The present invention relates to needles for performing an anesthesia procedure.

The body of a patient has a circumferential tissue layer termed the dura mater surrounding the spinal cord, and a space termed the subarachnoid space between the dura mater and spinal cord filled with cerebrospinal fluid. The dura mater is surrounded by an outer layer of tissue termed the ligamentum flavum.

There are two commonly known types of regional anesthesia procedures, the spinal anesthesia procedure and the epidural anesthesia procedure. In the spinal anesthesia procedure, a thin needle with stylet is pushed through the two layers below the spinal cord into the subarachnoid space, the stylet is removed and proper positioning of the needle is determined by cerebrospinal fluid passing out through the needle hub. Once the needle is in proper position, a suitable drug is injected through the needle which affects the spinal cord nerves and interrupts the ability of the spinal cord to transmit information. 20 In the epidural anesthesia procedure, a needle containing a stylet is pushed into the body until it contacts the ligamentum flavum which can be felt by an experienced physician. The stylet is then removed from the needle, and a syringe is attached to the needle. The needle is then advanced while pushing on the syringe plunger. When the needle passes through the ligamentum flavum, the plunger falls since there is a loss of resistance when the needle tip is located between the ligamentum flavum and the dura mater, at which time the dura mater is pushed away from the ligamentum flavum creating a space, termed the epidural space. Once the tip of the needle is properly positioned in the epidural space, the syringe is removed from the needle, and an epidural catheter is fed through the needle into the epidural space. The needle is removed from the catheter, and an anesthetic solution can be periodically introduced or inJected through the catheter into the epidural space in a continuous manner for an extended length of time.

In the spinal procedure, a small quantity of drug is injected into the subarachnoid space which provides a period of regional pain relief. In order to accomplish the same result in the epidural procedure, it is necessary to inject approximately 10 times the amount of drug used in the spinal procedure. The drug in the epidural space seeps through the dura mater to reach the spinal cord.

A much larger needle is utilized in the epidural procedure than the needle in the spinal procedure. A relatively small needle is required in the spinal procedure, so as to prevent the leakage of cerebrospinal fluid when the needle is removed from the dura mater. If the larger epidural needle is passed through the dura mater, the needle causes such a large opening that the cerebrospinal fluid will subsequently leak through the dura mater which lowers the quantity of cerebrospinal fluid in the cranium which, may result in a severe headache for an extended period of time. Hence, the limited lumen size of the spinal needle makes it difficult to pass a small catheter through the needle into the subarachnoid space.

The difficulty with the spinal procedure is that if the operation is too long, the effect of the drug wears off, and it is not normally possible to perform the procedure again. Hence, another form of anesthesia is then required, such as a general anesthesia in which the patient is placed on a respirator machine which is a difficult complication during the operation.

The main difficulty with the epidural procedure is that it is hard to accomplish without extensive experience by the physician. It is difficult to locate the epidural space, and the physician may accidently puncture the dura mater during the epidural procedure.

Some attempts have been made to place a catheter into the subarachnoid space to perform a continuous spinal anesthesia procedure. Some of these attempts are disclosed in the following publications:

Continuous Caudal Analgesia to Produce Painless Childbirth, J. Indian M.A., Vol. 63, No. 1, July 1, 1974, pp38, Continuous Procaine Spinal Anesthesia for Cesarian Section, Anesthesia and Analgesia, Vol. 51, No. 1, Jan.-Feb., 1972, pp117, Methemoglobinemia and Infant Response to Lidocaine and Prilocaine in Continuous Caudal Anesthesia: a Double - Blind Study, Anesthesia and Analgesia, Vol. 48, No. 5, Sept.-Oct., 1969, pp824, Experiences with Continuous Spinal Anesthesia in Physical Status Group IV Patients, Anesthesia and Analgesia, Vol. 47, No. 1, Jan.-Feb., 1968, pp18, Continous Spinal Anesthesia with Hypobaric Tetracaine for Hip Surgery in Lateral Decubitus, Anesthesia and Analgesia, Vol. 51, No. 5, Sept.-Oct., 1972, pp766, Spinal Subdural Hematoma Associated with Attempted Epidural Anesthesia and Subsequent Continuous Spinal Anesthesia, Anesthesia and Analgesia, Vol. 59, No. 1, Jan. 1980, pp72, Continuous Caudal Analgesia in Obstetrics, Proc. Roy. Soc. Med. Vol. 26, Feb. 1969, pp185, Continuous Caudal Epidural and Subarachnoid Anesthesia in Mares; a Comparative Study, Am. J. Vet. Res., Vol. 44, No. 12, pp2290, The Strange Case of the (Inadvertent) Continuous Spinal, John Sherratt & Son Ltd., pp82, The position of Plastic Tubing in Continuous - Block Techniques, an X-ray Study of 552 Patients, Anesthesiology, Sept.Oct., 1968, pp1047, Experience Cliniche Sulla Anesthesia Spinale Continua, Acta Anesthesiologica, 1968, pp49 and Raquiancstosia Continua Em Pacientes de Idadea Idadea Avancada, Rivsta Brasilcira de Anestesiologia, Ano 20, N. 4, Out-Dez. -1970, pp518.

However, in such procedures there is difficulty with the size of the needle and catheter. The relatively thin needle is relatively weak, and may bend. Also, it is difficult to thread the relatively small catheter through the needle.

SUMMARY OF THE INVENTION

The principal feature of the present invention is the provision of an improved needle for performing a spinal anesthesia procedure.

The needle of the present invention comprises, a proximal hollow hub, a first elongated tubular portion extending from the hub of a first larger diameter, and a second elongated tubular end portion located distal the first tubular portion of a second smaller diameter, with the outer diameter of the second tubular portion being in the range of approximately 0.018 to 0.025 inches, and the respective inner diameter of the second tubular portion being in the range of approximately 0.010 to 0.017 inches.

A feature of the present invention is that the second tubular portion has a sufficiently small outer diameter to safely puncture the dura mater without significant leakage of cerebrospinal fluid when the needle is removed from the dura mater.

Another feature of the present invention is that the needle may be utilized in a continuous spinal anesthesia procedure.

Still another feature of the invention is that the needle is stronger then those previously used for a continuous spinal anesthesia procedure.

Yet another feature of the invention is that a relatively small catheter may be threaded through the needle in a simplified manner as compared to other needles utilized for a continuous spinal anesthesia procedure.

Another feature of the invention is that the needle may be used for a spinal anesthesia procedure without the need for a catheter.

Further features will become more fully apparent in the following description of the embodiments of this invention and from the appended claims.

DESCRIPTION OF THE DRAWINGS

In the drawings:

FIG. 1 is a diagrammatic view of a portion of a patient's body in the region of the spinal cord;

FIG. 2 is a fragmentary elevational view of a needle of the present invention containing a stylet;

FIG. 3 is a fragmentary sectional view of the needle and a portion of the stylet of FIG. 2;

FIG. 4 is a fragmentary elevational view of the needle containing a catheter;

FIG. 5 is a fragmentary elevational view showing the catheter utilized in a continuous spinal anesthesia procedure;

FIG. 6-9 are sectional views of alternative embodiments of the needle of the present invention.

DESCRIPTION OF THE PREFERRED EMBODIMENTS

Referring now to FIG. 1, there is shown the spinal cord C of a patient, and the layer D termed the dura mater surrounding the spinal cord C and defining the subarachnoid space S between the dura mater D and spinal cord C and retaining cerebrospinal fluid CSF. A layer termed the ligamentum flavum L surrounds the dura mater D, and defines a spaced termed the epidural space E between ligamentum flavum L and the dura mater D. This space is formed when the dura mater is moved away from the ligamentum flavum.

Referring now to FIG. 2 and 3, there is shown the stepped needle generally designated 10 of the present invention. The needle 10 has a proximal hollow hub 12, and a first elongated tubular portion 14 of a first larger uniform diameter extending distally from and connected to the hub 12. The needle 10 has a second elongated tubular end portion 16 located distal the first tubular portion 14 and being of a smaller uniform diameter than the first tubular portion 14. The needle 10 preferably has an intermediate portion 18 which tapers from the first tubular portion 11 to the second tubular portion 16. The second tubular portion 16 has a beveled tip 20 to facilitate passage of the needle 10 through the body tissue.

The second tubular portion 16 has an outer diameter in the range of approximately 0.018 to 0.025 inches, and a respective inner 15 diameter being in the range of approximately 0.010 to 0.017 inches. The minimum length of the second tubular portion 16 is in the range of approximately ¼ to ¾ inches to accommodate the thickness of the ligamentum flavum L and dura mater D. The outer diameter of the first tubular portion 14 is in the range of approximately 0.025 to 0.050 inches, and the respective inner diameter of the first tubular portion is in the range of approximately 0.017 to 0.024 inches. The lengths of the first tubular portion 14, the intermediate portion 18, and the second tubular portion 16 may be approximately 3 ½ inches.

As shown in FIGS. 2 and 3, a stylet 22 is received in the needle 10, and has an elongated rod 24 extending through the hub 12, the first tubular portion 14, the intermediate portion 18, and the second tubular portion 16. The stylet 22 has a beveled tip 26 which is flush with the beveled tip 20 of the needle 10. As shown in FIG. 9, the rod 24 may have an proximal enlarged first portion 60 with an outer diameter approximately equal to the inner diameter of the first needle portion 14, and a second distal smaller portion 62 with an outer diameter approximately equal to the inner diameter of the second needle portion 16. In this manner, the stylet 22 adds additional strength to the needle 10 during use.

In use, the needle 10 is advanced through the body tissue of a patient with the stylet 22 in place until the needle tip 20 passes through the dura mater D and is located in the subarachnoid space S below the spinal cord C. The correct positioning of the needle tip 20 can be verified by removing the stylet 22 from the needle 10 in which case cerebrospinal fluid CSF will flow out through the needle hub 12. The tapered intermediate portion 18 facilitates passage of the needle 10 through the body tissue, and the elongated first tubular portion 14 provides additional strength to the needle 10 while it is being passed through the body tissue.

Once the needle 10 is in proper position, the stylet 22 is removed from the needle 10. Next, with reference to FIG. 4, a threading device 20 having an elongated hollow proximal end portion 30 and a hollow distal tubular section 32 of smaller diameter is positioned in the needle hub 12. An elongated thin catheter 34, such as plastic, having a lumen 36 is then passed through the threading device 28, the hub 12, the first tubular portion 14, the intermediate portion 18, and the second tubular portion 16 into the subarachnoid space S. The threading device 28 prevents kinking of the catheter 34 in the hub 12 during the passage of the catheter 34 through the hub 12. Also, the enlarged first tubular portion 14 facilitates passage of the thin catheter 34 through the needle 10. The catheter 34 has an outer diameter of at least 0.002 inches less than the inner diameter of the second tubular portion 16 in order to permit sufficiently free passage to the catheter 34 through the second tubular portion 16. The catheter 34 preferably has a wall thickness of 0.0015 inches.

Once the catheter 34 is in place, the threading device 28 and needle 10 are removed from the body tissue and from the catheter 34. The relatively small second tubular portion 16 of the needle 10 makes a sufficiently small opening in the dura mater D such that the opening will close and prevent leakage of cerebrospinal fluid CSF after the procedure is completed. An adapter 38 of known type, such as the adapter disclosed in U.S. Pat. No. 4,187,848, incorporated herein by reference, is then attached to the proximal end of the catheter 34 outside the patient's body, and a syringe 40 is attached to the catheter 38. A suitable drug is then periodically introduced by the syringe 30 through the adapter 38 and catheter 34 into the subarachnoid space S in order to perform a continuous spinal anesthesia procedure.

The advantages of the continuous spinal anesthesia procedure over the continuous epidural procedure are summarized below.

| CONTINUOUS EPIDURAL | CONTINUOUS SPINAL |
| --- | --- |
| Difficult catheter placement, | Rapid catheter placement. |
| Uncertain drug dosage since relying on seepage of the drug through the dura mater D. | Precise drug dosage. |
| Uncertain onset of drug reaction. | Immediate onset of drug reaction |
| Large dose maintenance required during procedure. | Low dose maintenance required during procedure. |
| Large needle used such as to pose risk of dural puncture headache. | Small needle used reduces risk of dural puncture headache to a minimum. |

Another embodiment of the present invention is illustrated in FIG. 6, in which like reference numerals designate like parts. In this embodiment, the needle 10 has an intermediate tubular portion 42 of uniform diameter between the first tubular portion 14 and second tubular portion 16 which are the same as previously described. The intermediate portion 42 has an outer and inner diameter of a size between the respective diameters of the first tubular portion 14 and second tubular portion 16.

Another embodiment of the invention is illustrated in FIG. 7, in which like reference numerals designate like parts. In this embodiment, the needle 10 has a tubular portion 44 which tapers from a proximal end 46 of the tubular portion to the tip 20. The tip 20 has inner and outer diameters in the range of the respective diameters of the second tubular portion 16 described in connection with FIGS. 1-5, and the proximal end 46 has inner and outer diameters in the range of the first tubular portion 14 described in connection with FIGS. 1-5. As shown, the lumen 48 of the tubular portion 44 may also be tapered from the proximal end 46 to the tip 20.

Another embodiment of the present invention is illustrated in FIG. 8, in which like reference numerals designate like parts. In this embodiment, the needle 10 is tapered from the first tubular portion 14 to the tip 20, with the tip 20 having outer and inner diameters in the same range as the second tubular portion 16 previously described in connection with FIGS. 1-5, and with the first tubular portion 14 having outer and inner diameters in the same range as the first tubular portion 14 described in connection with FIGS. 1-5. As shown, the lumen 48 of the needle 10 may also taper from the first tubular portion 14 to the tip 20.

In an alternative form, the catheter 34 may be made of a suitable metallic material, such as stainless steel, type 304. The metallic catheter 34 has less chance of kinking than the plastic catheter, and less chance of being cut by the needle tip which might otherwise leave a piece of the catheter in the patient's body. The outer diameter of the metallic catheter 34 may be as small as 0.006 inches, in which case the needle tip has an inner diameter as small as 0.008 inches and an outer diameter of approximately 0.016 inches. The outer diameter of the tip is in the range of approximately 0.016 to 0.025 inches, and the respective inner diameter of the tip is in the range of approximately 0.008 to 0.017 inches. The outer diameter of the metallic catheter is in tho range of approximately 0.006 to 0.015 inches.

Further features will become more fully apparent in the following description of the embodiments of this invention and from the appended claims.

What is claimed is:

1. A needle, comprising:
a proximal hollow hub;
a first elongated tubular portion extending from the hub of a first diameter; and
a second elongated tubular portion located distal the first tubular portion, said second tubular portion being tapered on the outside thereof from the first tubular portion to a tip at a distal end of the second tubular portion, with the tip having an outer diameter in the range of approximately 0.018 to 0.025 inches, and the tip having an inner diameter in the range of approximately 0.010 to 0.017 inches.

2. The needle of claim 1 wherein the inside of the second tubular portion tapers from the first tubular portion to the tip.

3. The needle of claim 1 wherein the first tubular portion has an outer diameter in the range of approximately 0.025 to 0.050 inches, and the first tubular portion has a respective inner diameter in the range of 0.017 to 0.042 inches.

* * * * *